United States Patent [19]

Haga et al.

[11] Patent Number: 4,861,886

[45] Date of Patent: Aug. 29, 1989

[54] METHOD FOR ISOMERIZATION OF TRANS-FORM 2-METHYLSPIRO (1,3-OXATHIOLANE-5,3')QUINUCLIDINE OR ACID ADDITION SALTS THEREOF

[75] Inventors: Takahiro Haga; Itaru Shigehara; Toru Koyanagi; Kazutoshi Hara; Masaru Maeda, all of Kusatsu, Japan

[73] Assignee: Ishahara Sangyo Kaisha Ltd, Osaka, Japan

[21] Appl. No.: 215,532

[22] Filed: Jul. 6, 1988

[30] Foreign Application Priority Data

Jul. 10, 1987 [JP] Japan .................................. 62-172451
Jul. 21, 1987 [JP] Japan .................................. 62-180119
Aug. 13, 1987 [JP] Japan .................................. 62-202170
Jan. 18, 1988 [JP] Japan .................................. 63-7020

[51] Int. Cl.$^4$ .......................................... C07D 495/20
[52] U.S. Cl. .................................................... 546/16
[58] Field of Search ........................................ 546/18

[56] References Cited

U.S. PATENT DOCUMENTS 4,054,582 10/1977 Blanchard et al. .................. 549/391

FOREIGN PATENT DOCUMENTS 0062979 10/1982 European Pat. Off. ............ 540/128
0205247 12/1986 European Pat. Off. ............. 546/18
2227504 1/1974 Fed. Rep. of Germany ...... 562/553

OTHER PUBLICATIONS

Chemical Abstract, vol. 78, No. 19, May 14, 1973, pp. 463, abstract no. 124365c, E. A. Karakhanov et al.

*Primary Examiner*—Robert T. Bond
*Attorney, Agent, or Firm*—Oblon, Spivak, McClelland, Maier & Neustadt

[57] ABSTRACT

A method for isomerization of trans-form 2-methylspiro(1,3-oxathiolane-5,3')quinuclidine or acid addition salts thereof, which comprises isomerizing said trans-form quinuclidine or acid addition salts thereof to cis-form 2-methylspiro(1,3-oxathiolane-5,3')quinuclidine or acid addition salts thereof in the presence of at least one acid catalyst selected from the group consisting of an organic sulfuric acid, a halide functioning as a Lewis acid, and sulfuric acid.

10 Claims, No Drawings

METHOD FOR ISOMERIZATION OF TRANS-FORM 2-METHYLSPIRO (1,3-OXATHIOLANE-5,3')QUINUCLIDINE OR ACID ADDITION SALTS THEREOF

The present invention relates to a method for isomerization of trans-form 2-methylspiro(1,3-oxathiolane-5,3')quinuclidine (hereinafter referred to simply as T-MSOQ) or acid addition salts thereof. More particularly, it relates to a method for isomerizing T-MSOQ or acid addition salts thereof to cis-form 2-methylspiro(1,3-oxathiolane-5,3')quinuclidine (hereinafter referred to simply as C-MSOQ) or acid addition salts thereof in the presence of a certain acid catalyst. C-MSOQ or acid addition salts thereof obtainable by this isomerization reaction are useful for the treatment of diseases of the central nervous system in mammals, particularly for the treatment of diseases due to disturbances of central cholinergic function.

C-MSOQ or acid addition salts thereof referred to in this invention are disclosed in EP 205,247A. This publication also discloses a method wherein 3-hydroxy-3-mercaptomethylquinuclidine and acetaldehyde are subjected to a cyclization reaction in the presence of borontrifluoride etherate to obtain 2-methylspiro(1,3-oxathiolane-5,3')quinuclidine (hereinafter referred to simply as MSOQ) or acid addition salts thereof, followed by fractional crystallization to obtain C-MSOQ or acid addition salts thereof, but does not disclose or suggest the isomerization of T-MSOQ or acid addition salts thereof to obtain C-MSOQ or acid addition salts thereof.

Noting that during the preparation of MSOQ or acid addition salts thereof, geometrical isomers i.e. T-MSOQ or acid addition salts thereof and C-MSOQ or acid addition salts thereof are formed, and among them C-MSOQ or acid addition salts thereof are effective for the treatment of diseases of the central nervous system in mammals, particularly for the treatment of diseases due to disturbances of central cholinergic functions, the present inventors have paid a particular attention to conversion of T-MSOQ or acid addition salts thereof to C-MSOQ or acid addition salts thereof.

The present inventors have conducted extensive research by using various catalysts to convert T-MSOQ or acid addition salts thereof to C-MSOQ or acid addition salts thereof and as a result, have found that when a certain acid catalyst is used, isomerization of T-MSOQ or acid additions salts thereof to C-MSOQ or acid addition salts thereof can readily be accomplished. The present invention has been accomplished on the basis of this discovery.

The present invention provides a method for isomerization of trans-form 2-methylspiro(1,3-oxathiolane-5,3')quinuclidine or acid addition salts thereof, which comprises isomerizing said trans-form quinuclidine or acid addition salts thereof to cis-form 2-methylspiro(1,3-oxathiolane-5,3')quinuclidine or acid addition salts thereof in the presence of at least one acid catalyst selected from the group consisting of an organic sulfonic acid, a halide functioning as a Lewis acid, and sulfuric acid.

Now, the present invention will be described in detail with reference to the preferred embodiments.

MSOQ is represented by the following formula:

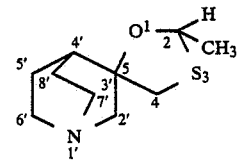

This includes geometrical isomers i.e. T-MSOQ and C-MSOQ. In T-MSOQ, the methyl group at the 2-position on the 1,3-oxathiolane ring and the nitrogen atom at the 1'-position of the quinuclidine ring are located at the opposite sides of the plane of the 1,3-oxathiolane ring. Whereas, in C-MSOQ, the methyl group at the 2-position and the nitrogen atom at the 1'-position are located on the same side of the plane of 1,3-oxathiolane ring. T-MSOQ and C-MSOQ have mirror-image isomers, respectively.

For the purpose of the present invention, the acid addition salts may be inorganic or organic salts such as salts of sulfuric acid, phosphoric acid, hydrochloric acid, hydrobromic acid, hydroiodic acid, sulfamic acid, methansulfonic acid, benzenesulfonic acid, p-toluenesulfonic acid, acetic acid, lactic acid, succinic acid, maleic acid, tartaric acid, citric acid, gluconic acid, ascorbic acid, benzoic acid and cinnamic acid.

The organic acid as an acid catalyst used in the method of the present invention, may be a sulfonic acid of the formula $R\text{-}SO_3H$ wherein R is an alkyl group, an alkenyl group, an alkynyl group or an aryl group, or a polymeric organic sulfonic acid. The alkyl group, the alkenyl group and the alkynyl group for R may be straight chained or branched with from 1 to 20 carbon atoms, and a part or whole of their hydrogen atoms may be substituted by halogen atoms such as fluorine. The aryl group for R includes a phenyl group or a naphthyl group, which may be substituted by substituents selected from the group consisting of an alkyl group, a trifluoromethyl group, a halogen atom, a nitro grop and a cyano group. The organic sulfonic acid of the above formula includes, for example, methane sulfonic acid, ethane sulfonic acid, vinyl sulfonic acid, acetylene sulfonic acid, camphor sulfonic acid, trifluoromethane sulfonic acid, benzene sulfonic acid, p-toluene sulfonic acid, p-chlorobenzene sulfonic acid, dodecylbenzene sulfonic acid and naphthalene sulfonic acid. The polymeric organic sulfonic acid includes, for example, a fluorine resin such as a polytetrafluoroethylene resin having sulfonic acid groups. Specifically, NAFION (NAFION NR-50, tradename, manufactured by Du Pont Company) may be mentioned. Among them, an organic sulfonic acid of the above formula wherein R is an aryl group is preferred from the industrial point of view.

The halide functioning as a Lewis acid as the acid catalyst includes, for example, halides of e.g. boron, aluminum, titanium, iron, zinc and antimony. Specifically, boron trifluoride, boron trichloride, boron tribromide, aluminum chloride, aluminum bromide, titanium tetrachloride, ferric chloride, zinc chloride, or antimony pentachloride may be mentioned. Among them, boron trifluoride, aluminum chloride and ferric chloride are preferred from the industrial point of view.

The sulfuric acid as the acid catalyst usually has a concentration of from 5 to 90%, preferably from 20 to 80%.

The acid catalyst is used usually in an amount of from 0.1 to 10 moles, preferably from 0.2 to 5 moles, per mole of T-MSOQ or acid addition salts thereof. However, in a case where the acid catalyst used forms a salt with T-MSOQ, it will be necessary to use an additional amount necessary for the formation of the salt.

To conduct the method for isomerization of the present invention, it is usual that T-MSOQ or acid addition salts thereof and the acid catalyst are mixed, and if necessary, a solvent is added thereto.

As such a solvent, any solvent may be used so long as it does not adversely affect the isomerization reaction of the present invention.

When the organic sulfonic acid is used as the acid catalyst, the solvent may be water, a hydrophilic organic solvent or a hydrophobic organic solvent. Specifically, it includes water; ketones such as methyl ethyl ketone and methyl isobutyl ketone; aliphatic hydrocarbons such as hexane and cyclohexane; halogenated hydrocarbons such as methylene chloride, chloroform and 1,2-dichloroethane; aromatic hydrocarbons such as benzene and toluene; ethers such as diethyl ether, tetrahydrofuran and dioxane; esters such as methyl acetate and ethyl acetate; and aprotic polar solvents such as dimethylformamide and dimethylsulfoxide. They may be used alone or in combination as a mixture. Among them, a hydrophobic organic solvent such as an aliphatic hydrocarbon or aromatic hydrocarbon is preferred.

When the halide functioning as the Lewis acid is used as the acid catalyst, a hydrophobic organic solvent may be employed. Specifically, the above-mentioned aliphatic hydrocarbons, halogenated hydrocarbons and aromatic hydrocarbons may be employed. Among them, halogenated hydrocarbons are preferred.

When sulfuric acid is used as the acid catalyst, water is employed as the solvent.

The isomerization reaction is conducted usually within a temperature range of from 0° to 150° C., preferably from 40° to 130° C. for from 0.2 to 48 hours. The isomerization reaction is followed by usual work up.

According to the method of the present invention, about 20% or more of T-MSOQ or acid addition salts thereof can be isomerized to C-MSOQ or acid addition salts thereof. Further, by properly adjusting the reaction conditions, the isomerization ratio can be improved.

The reaction product after completion of the isomerization may be withdrawn as an oily substance of MSOQ, or may be converted to an acid addtion salt of MSOQ in order to obtain stable crystal. For example, in the case of conversion to the hydrogen chloride salt, MSOQ as the reaction product is dissolved in a suitable solvent, to which hydrogen chloride is introduced, or an isopropyl alcohol solution of hydrogen chloride is added, whereby the disired hydrogen chloride salt will be obtained.

MSOQ or acid addition salts thereof in the reaction product after completion of the isomerization, is withdrawn as described above, and then C-MSOQ or acid addition salts thereof can readily be isolated by an operation for separation such as fractional crystallization.

Now, the present invention will be described with reference to some Examples. However, it should be understood that the present invention is by no means restricted to such specific Examples.

EXAMPLE 1

Into a 10 ml round-bottom flask equipped with a reflux condenser, 1.18 g of T-MSOQ hydrochloride, 1.9 g of p-toluene sulfonic acid monohydrate and 1.9 g of water were charged and stirred by a stirrer at room temperature. The mixture was then gradually heated in an oil bath and then reacted at 80° C. for two hours. After completion of the reaction, the reaction product was analysed by high performance liquid chromatography, whereby the molar fraction of C-MSOQ was 51.9% (isomerization ratio).

EXAMPLE 2

Into a 20 ml round-bottom flask equipped with a reflux condenser, 3.0 g of T-MSOQ, 5.72 g of p-toluene sulfonic acid monohydrate and 5.72 g of water were charged and stirred by a stirrer at room temperature. The mixture was gradually heated in an oil bath and then reacted at 80° C. for 6 hours. After completion of the reaction, this reaction product was analysed by high performance liquid chromatography, whereby the molar fraction of C-MSOQ was 26.3% (isomerization ratio).

EXAMPLE 3

Into a 50 ml round-bottom flask equipped with a Dean-Stark trap, a reflux condenser and a calcium chloride tube, 603 mg of trifluoromethane sulfonic acid and 20 ml of benzene were added, refluxed for 20 minutes and then left to cool for 5 minutes. To this mixture, 400 mg of T-MSOQ was added, and the mixture was reacted at a reflux temperature for 20 minutes. After completion of the reaction, the reaction product was analysed by high performance liquid chromatography, whereby the molar fraction of C-MSOQ was 50% (isomerization ratio).

EXAMPLE 4

Into a 50 ml round-bottom flask equipped with a Dean-Stark trap, a reflux condenser and a calcium chloride tube, 0.77 g of methanesulfonic acid and 40 ml of benzene were added, refluxed for 20 minutes and then left to cool for 5 minutes. To this mixture, 0.8 g of T-MSOQ was added, and the mixture was reacted at a reflux temperature for two hours. After completion of the reaction, this reaction product was analysed by high performance liquid chromatography, whereby the molar fraction of C-MSOQ was 25% (isomerization ratio).

EXAMPLE 5

Into a 50 ml round-bottom flask equipped with a Dean-Stark trap, a reflux condenser and a calcium chloride tube, 1.53 g of p-toluene sulfonic acid monohydrate, 40 ml of benzene and 0.8 g of T-MSOQ were charged and reacted for one hour while azeotropically dehydrating at a reflux temperature. After completion of the reaction, this reaction product was analysed by high performance liquid chromatography, whereby the molar fraction of C-MSOQ was 19.2% (isomerization ratio).

EXAMPLES 6 to 9

The reactions were conducted in the same manner as in Example 5 under the reaction conditions as indentified in Table 1. The results are shown in Table 1.

TABLE 1

| Example No. | Amount (g) of T-MSOQ | Type and amount (g) of acid catalyst | Type and amount (ml) of solvent | Reaction temperature | Reaction time (hr) | Molar fraction (%) of C-MSOQ in reaction product (isomerization ratio) |
| --- | --- | --- | --- | --- | --- | --- |
| 6 | 10 | p-Toluene sulfonic acid monohydrate 19.1 | Toluene 50 | Reflux temperature | 3 | 48 |
| 7 | 10 | " 19.1 | Hexane 40 | Reflux temperature | 10 | 50 |
| 8 | 1 | " 1.9 | Chloroform 50 | Reflux temperature | 24 | 22.3 |
| 9 | As HCl salt 11.8 | " 19.1 | Toluene 50 | Reflux temperature | 3 | 48 |

EXAMPLE 10

Into a 20 ml round-bottom flask equipped with a reflux condenser, 3.0 g of T-MSOQ hydrogen chloride and 9 ml of a 50% sulfuric acid aqueous solution comprising equal weight amounts of conc-sulfuric acid and water were charged and stirred by a stirrer at room temperature. The mixture was gradually heated in a warm water bath and then reacted at a temperature of from 50° to 60° C. for 30 minutes.

After completion of the reaction, the reaction product was changed to alkaline by an addition of 40 ml of a 20% sodium hydroxide aqueous solution while cooling with ice water and then extracted four times with n-hexane. The extracted layer thus obtained was dried by an addition of 5 g of anhydrous sodium sulfate to obtain 40 ml of a n-hexane solution containing 2.0 g of MSOQ.

This solution was analysed by high performance liquid chromatography, whereby the molar fraction of C-MSOQ was 52.7% (isomerization ratio).

REFERENCE EXAMPLE 1

40 ml of n-hexane solution containing 2.0 g of MSOQ obtained in the same manner as in Example 10 was adjusted to pH 4 by an addition of 3.5 ml of a 4N hydrogen chloride isopropyl alcohol solution. Crystals thereby formed were collected by filtration and vacuum-dried at 40° C. over a period of 8 hours to obtain 2.2 g of MSOQ hydrogen chloride.

EXAMPLES 11 to 15 and REFERENCE EXAMPLES 2 to 6

The reactions were conducted in the same manner as in Examples 10 and Reference Example 1 under the reaction conditions as identified in Table 2. The results are shown in Table 2.

TABLE 2

| Example No. | Amount (g) of T-MSOQ hydrogen chloride | Type and amount (g) of acid catalyst | Reaction temperature (°C.) | Reaction time (hr) | Molar fraction (%) of C-MSOQ (isomerization ratio) | Reference Example No. | Amount (g) of obtained MSOQ hydrogen chloride |
| --- | --- | --- | --- | --- | --- | --- | --- |
| 11 | 5.0 | 20% sulfuric acid 57.6 | 100 | 1.25 | 51.2 | 2 | 2.37 |
| 12 | 5.0 | 40% sulfuric acid 27.4 | 50–60 | 1 | 53.4 | 3 | 3.61 |
| 13 | 5.0 | 80% sulfuric acid 8.21 | 20–25 | 1 | 53.7 | 4 | 3.01 |
| 14 | 5.0 | 40% sulfuric acid 5.47 | 50–60 | 7 | 48.2 | 5 | 2.70 |
| 15 | 5.0 | 40% sulfuric acid 50.7 | 40–50 | 3 | 44.5 | 6 | 2.86 |

EXAMPLE 16

1.06 g of ferric chloride was added to 20 ml of a chloroform solution containing 1 g of T-MSOQ under a nitrogen stream, and the mixture was reacted at room temperature (30° C.) for 3.5 hours under stirring.

After completion of the reaction, 10 ml of a 10% sodium hydroxide aqueous solution was added thereto, followed by liquid separation. The aqueous layer thus obtained was extracted twice with 10 ml of chloroform. The chloroform layers were put together, washed with 10 ml of water and dried by an addition of 1 g of anhydrous sodium sulfate. After drying, chloroform was distilled off under reduced pressure to obtain 0.54 g of MSOQ.

This product was analysed by high pressure liquid chromatography, whereby the molar fraction of C-MSOQ was 52% (isomerization ratio).

REFERENCE EXAMPLE 7

0.54 g of MSOQ obtained in Example 16 was dissolved in 30 ml of hexane, and a 5N hydrogen chloride isopropyl alcohol solution was added thereto until the pH became 3, whereby 0.46 g of crystals of MSOQ hydrogen chloride were obtained.

EXAMPLES 17 and 18

The reactions were conducted in the same manner as in Example 16 under the reaction conditions as identified in Table 3. The results are shown in Table 3.

TABLE 3

| Example No. | Amount (g) of T-MSOQ hydrogen chloride | Type and amount (g) of acid catalyst | Type and amount (g) of solvent | Reaction temperature (°C.) | Reaction time (hr) | Molar fraction of C-MSOQ in reaction product (isomerization ratio) |
|---|---|---|---|---|---|---|
| 17 | 2.36 | AlCl$_3$ 2 | Chloroform 20 | 40 | 1.5 | 51.7 |
| 18 | 2.00 | BF$_3$ 2.9 | Chloroform/ Dimethyl- sulfoxide (20/1) 42 | 25 | 26 | 51.5 |

We claim:

1. A method for isomerization of trans-form 2-methylspiro(1,3-oxathiolane-5,3')quinuclidine or acid addition salts thereof which comprises isomerizing said trans-form quinuclidine or acid addition salts thereof to cis-form 2-methylspiro(1,3-oxathiolane-5,3')quinuclidine or acid addition salts thereof in the presence of at least one acid catalyst selected from the group consisting of an organic sulfonic acid, a halide functioning as a Lewis acid, and sulfonic acid.

2. The method according to claim 1, wherein the acid catalyst is used in an amount of from 0.1 to 10 mols per mol of said trans-form quinuclidine or acid addition salts thereof.

3. The method according to claim 1, wherein the isomerization is conducted in the presence of a solvent.

4. The method according to claim 1, wherein the isomerization is conducted at a temperature of from 0° to 150° C.

5. The method according to claim 1, wherein the acid catalyst is at least one member selected from the group consisting of organic sulfonic acids.

6. The method according to claim 1, wherein the acid catalyst is at least one member selected from the group consisting of organic sulfonic acids, and the isomerization is conducted in the presence of a hydrophobic organic solvent.

7. The method according to claim 6, wherein the hydrophobic organic solvent is an aromatic hydrocarbon or an aliphatic hydrocarbon.

8. The method according to claim 1, wherein the acid catalyst is sulfuric acid, and the isomerization is conducted in the presence of water.

9. The method according to claim 8, wherein the concentration of sulfuric acid is from 5 to 90%.

10. The method according to claim 1, wherein the acid catalyst is a halide functioning as a Lewis acid, and the isomerization is conducted in the presence of a hydrophobic organic solvent.

* * * * *